(12) United States Patent
Lee

(10) Patent No.: US 10,519,414 B2
(45) Date of Patent: Dec. 31, 2019

(54) APPARATUS AND METHOD FOR CONTINUOUS CELL CULTURE

(71) Applicant: MEDIKAN INC, Seoul (KR)

(72) Inventor: Hee Young Lee, Seoul (KR)

(73) Assignee: MEDIKAN INC, Seoul (KR)

(*) Notice: Subject to any disclaimer, the term of this patent is extended or adjusted under 35 U.S.C. 154(b) by 409 days.

(21) Appl. No.: 15/027,751

(22) PCT Filed: Oct. 16, 2014

(86) PCT No.: PCT/KR2014/009714
§ 371 (c)(1),
(2) Date: Apr. 7, 2016

(87) PCT Pub. No.: WO2015/056986
PCT Pub. Date: Apr. 23, 2015

(65) Prior Publication Data
US 2016/0237392 A1  Aug. 18, 2016

(30) Foreign Application Priority Data

Oct. 16, 2013  (KR) .......................... 10-2013-0123459
Oct. 16, 2014  (KR) .......................... 10-2014-0139677

(51) Int. Cl.
*C12M 1/26* (2006.01)
*C12M 1/00* (2006.01)
(Continued)

(52) U.S. Cl.
CPC ............ *C12M 33/04* (2013.01); *C12M 23/24* (2013.01); *C12M 23/34* (2013.01); *C12M 23/38* (2013.01);
(Continued)

(58) Field of Classification Search
CPC ...... C12M 23/10; C12M 23/38; C12M 23/58; C12M 33/04; C12M 41/12; C12M 29/04;
(Continued)

(56) References Cited

U.S. PATENT DOCUMENTS 4,225,671 A * 9/1980 Puchinger et al. .... C07K 14/62
435/297.2
4,810,652 A * 3/1989 Witt ....................... C12M 23/44
15/211

(Continued)

FOREIGN PATENT DOCUMENTS

KR  10-2001-0029122 A  4/2001
KR  10-2011-0091078 A  8/2011

OTHER PUBLICATIONS

International Search Report of PCT/KR2014/009714, dated Feb. 27, 2015. [PCT/ISA/210].
(Continued)

*Primary Examiner* — Gautam Prakash
(74) *Attorney, Agent, or Firm* — Cantor Colburn LLP

(57) ABSTRACT

Disclosed is a method of continuously culturing cells, including culturing the cells by injecting a culture medium into an internal compartment of a sealed culture vessel and then inoculating the culture medium with the cells, detaching the adhered cells when the density of the cells cultured in the compartment of the culture vessel is a reference value or more, and obtaining the cells detached from the culture vessel, which is maintained in a sealed state.

7 Claims, 8 Drawing Sheets

(51) Int. Cl.
*C12M 1/04* (2006.01)
*C12M 1/34* (2006.01)
*C12N 5/00* (2006.01)

(52) U.S. Cl.
CPC .......... *C12M 23/58* (2013.01); *C12M 29/04* (2013.01); *C12M 33/00* (2013.01); *C12M 41/12* (2013.01); *C12M 41/40* (2013.01); *C12N 5/00* (2013.01); *C12N 2509/10* (2013.01)

(58) Field of Classification Search
CPC ...... C12M 23/34; C12M 23/24; C12M 41/40; C12M 33/00; C12N 5/00; C12N 2509/10
See application file for complete search history.

(56) References Cited

U.S. PATENT DOCUMENTS

| | | | |
|---|---|---|---|
| 5,409,841 A * | 4/1995 | Chow | A61L 2/10 422/24 |
| 5,882,918 A * | 3/1999 | Goffe | B01L 7/02 435/286.6 |
| 5,900,374 A | 5/1999 | Otto-Nagels | |
| 2003/0068814 A1 | 4/2003 | Malinge | |
| 2010/0015694 A1 | 1/2010 | Acosta | |
| 2010/0304472 A1* | 12/2010 | Kim et al. | C12M 23/08 435/304.1 |

OTHER PUBLICATIONS

Written Opinion of PCT/KR2014/009714, dated Feb. 27, 2015. [PCT/ISA/237].

* cited by examiner

APPARATUS AND METHOD FOR CONTINUOUS CELL CULTURE

CROSS REFERENCE TO RELATED APPLICATIONS

This application is a National Stage of International Application No. PCT/KR2014/009714 filed Oct. 16, 2014, claiming priorities based on Korean Patent Application Nos. 10-2013-0123459, filed Oct. 16, 2013 and 10-2014-0139677, filed Oct. 16, 2014, the contents of all of which are incorporated herein by reference in their entirety.

TECHNICAL FIELD

The present invention relates to a device and a method for continuously culturing cells and, more particularly, to a device and a method for continuously culturing cells including injection, culture, detachment, and obtaining of the cells and a culture medium while maintaining a seal.

BACKGROUND ART

Examples of cell culture include monolayer culture (adhesion culture), in which cells are adhered to incubators for propagation, and suspension culture, in which cells are propagated in a suspended state.

Most animal cells adhere to surfaces in order to grow and have a growth speed that is even slower than that of microorganisms, and accordingly, productivity is low and the animal cells are easily contaminated by microorganisms during culturing.

However, in cell plate adhesion culture, it is difficult to maintain a seal, and thus cells are easily contaminated after a cell obtaining process over a predetermined period of time in existing processes.

Further, a separate sealing unit needs to be provided when the cultured cells are moved to the outside of a laboratory, but there is no successful case where sealing is perfect, and vessels are mostly transported in order to move the cells.

However, when the vessels are transported, another passage occurs, thus making it difficult to maintain uniformity of the cultured cells.

Meanwhile, a protease such as trypsin is used to detach the cells that have adhered to the inside of the vessel to be cultured.

The enzyme dissolves the connection surface with the adhesion surface to destabilize adhesion of the cells, and entails various problems such as a long enzyme treatment time, changes in the properties of the cells and the death of cells owing to toxicity of the enzyme.

The extent of change in the properties of cells is classified based on a trypsin treatment number, which is evidence that the use of trypsin changes the properties of the cells.

Further, since the use of trypsin results in detachment of adhered cells from all surfaces of the culture vessel, a process for again adhering some of the cells is required after the use of trypsin, and the re-adhesion rate is low, namely 10% or less.

Examples of a process for preventing trypsin from being used include various processes such as a process of using the strong shear force of water, a scraping process in which a scraper is applied to a flat plate or a smoothly curved surface, a process of using temperature-reactive liquefaction/curable solid-liquid and liquid-solid materials as an adhesion material, and a process of using a collagenase instead of trypsin, but there are drawbacks in that the rate of cell recovery is low or inconsistent and in that a cell adhesion area is limited.

For example, in the case where the cells are detached from the cell adhesion beads using only the shear force of water, since a strong vortex must be used, the flow direction of water is not uniform, and accordingly, the recovery ratio is inconsistent, and the beads collide with each other, thus damaging cells sandwiched between the beads.

Further, in the case where the collagen adhesion material and the collagenase are used, since the enzyme does not affect cells positioned at the inside when the cells are layered in two or more layers, some of the cells may not be dissolved, or there is a risk of dissolving the cells owing to the function of the collagenase, which is similar to that of trypsin, during the period required to completely dissolve collagen, and accordingly, it is not easy to use the aforementioned technique.

DISCLOSURE

Technical Problem

Accordingly, the present invention has been made keeping in mind the above problems occurring in the related art, and an object of the present invention is to provide a device for continuously culturing cells and a culturing method using the same, in which the cells and a culture medium are selectively and repeatedly injected, cultured, detached, and obtained while a sealed state of a culture vessel is maintained, and accordingly, the cells are obtained while some of the cultured cells are allowed to remain during an obtaining process, thereby repeatedly culturing the cells remaining in the culture vessel, preventing the cultured cells from being contaminated, and attaining uniformity of the cultured cells.

Another object of the present invention is to supply an optimum culture temperature and a gas, required to propagate the cells, to a culture vessel using a culture environment unit, in which the culture vessel is stored and which provides an optimum culture environment for propagating the cells, thereby improving the efficiency of propagation of the cell culture.

A further object of the present invention is to detach cultured cells from the bottom of a compartment of a culture vessel in a sealed state.

Yet another object of the present invention is to use a sealing-type culture vessel to thus easily move, store, and manage cells.

Technical Solution

In order to accomplish the above objects, the present invention provides a device for continuously culturing cells, including a culture vessel having a compartment that is selectively determined to be sealed. A culture medium is injected into the compartment and inoculated with the cells and the cells are detached and obtained while the compartment is sealed, and the cells are cultured while the compartment is open.

According to the present invention, the cells are obtained while some of the cultured cells are excluded during a process of obtaining the cells so that the cells remaining in the culture vessel are repeatedly cultured.

According to the present invention, all of the cultured cells are obtained during a process of obtaining the cells, and then injection of the culture medium into the culture vessel, inoculation with the cells, and culturing, detaching, and obtaining of the cells are repeated.

According to the present invention, the culture vessel includes a sealing-type passageway through which fluid, gases, and the cells are moved from outside into the compartment or from the compartment to the outside.

According to the present invention, a circulation filter, through which a gas required to culture the cells is circulated into the compartment, is provided to the culture vessel.

According to the present invention, a scraper is provided in the compartment to scrape the cells using the movement of the scraper to thus detach the cells from the bottom surface of the compartment.

According to the present invention, a scraper is provided in the compartment to scrape the cells using the rotation of the scraper to thus detach the cells from the bottom surface of the compartment.

According to the present invention, one or more sealing-type passageways are provided on the surface of the culture vessel, the sealing-type passageways include soft blocks for sealing the compartment, the fluid, the gas, and the cells are moved out of or into the compartment through the passageways when a needle of a syringe is stuck into the compartment, and the compartment is sealed, owing to the elasticity of the sealing-type passageways, when the needle is removed.

According to the present invention, the gas moving out of or into the compartment to be circulated through the circulation filter includes one or more of carbon dioxide and oxygen.

According to the present invention, the circulation filter includes a conduit provided on a side surface of the culture vessel, a valve provided at an end of the conduit, and a filter provided in the valve.

According to the present invention, the culture vessel is stored in a culture environment unit, which maintains the temperature of the culture medium at 0 to 42° C. to culture biological cells.

According to the present invention, negative pressure is generated in a culture environment unit including the culture vessel stored therein to change the size of the compartment of the culture vessel to thus supply the gas required to culture the cells into the compartment in the culture environment unit through the circulation filter.

According to the present invention, one or more culture vessels are provided, and a plurality of culture vessels is continuously connected through the circulation filter to integrally circulate the gas.

According to the present invention, the scraper is moved using external potential energy.

According to the present invention, the scraper is rotated or moved while in contact with an internal surface of the compartment using external mechanical force to scrape the cells.

According to the present invention, the scraper is rotated or moved while in contact with the internal surface of the compartment using magnetic force to scrape the cells.

According to the present invention, the scraper includes a plurality of blades on the lower surface thereof, which comes into contact with the bottom surface of the compartment.

According to the present invention, a culture groove is formed on the scraper to be filled with a culture medium and culture the cell.

According to the present invention, the scraper is made of a material selected from polyethylene (PE), polypropylene (PP), polyamide (PA), polyacetal (POM), polyvinyl chloride (PVC), polyester (PET), polymethylpentene (PMP), an ionomer (IO), ethylene vinyl alcohol (EVOH), polystyrene (PS), a methacrylic resin (PMMA), polycarbonate (PC), polyvinyl acetate (PVAc), polyvinyl alcohol (PVA), a phenol resin (PF), a urea resin (UF), a melamine resin (MF), an epoxy resin (EP), polyurethane (PUR), an unsaturated polyester resin (UP), and a metal.

According to the present invention, when a moving member is moved close to the external lower surface of the culture vessel, the scraper and the moving member are linked using magnetic force.

According to the present invention, the scraper includes a plurality of blades on the lower surface thereof, which comes into contact with the bottom surface of the compartment, and the blades are formed so as to have an edge angle to thus detach the cells from the bottom surface by rubbing the bottom surface of the compartment.

According to the present invention, the scraper includes a plurality of blades on the lower surface thereof, which comes into contact with the bottom surface of the compartment, and the blades are formed so as to have continuous edge angles to thus come into contact or not come into contact with the bottom surface of the compartment.

According to the present invention, the circulation filter includes a clip provided around the conduit to selectively seal and open the conduit.

In order to accomplish the above objects, the present invention also provides a method of continuously culturing cells, including culturing the cells by injecting a culture medium into an internal compartment of a sealed culture vessel and then inoculating the culture medium with the cells, detaching the adhered cells when the density of the cells cultured in the compartment of the culture vessel is a reference value or more, and obtaining the cells detached from the culture vessel, which is maintained in a sealed state.

According to the present invention, the culturing of the cells includes injecting the culture medium into the compartment, inoculating the culture medium with the cells, and propagating the cells in the culture medium.

According to the present invention, the injecting of the culture medium, the inoculating of the culture medium with the cells, the detaching of the adhered cells, and the obtaining of the cells are performed while the vessel is always sealed so as to enable stable and repeated culture of the cells after the obtaining of the cells.

According to the present invention, the detaching of the adhered cell includes moving a scraper, provided in the compartment, using mechanical energy or potential energy to scrape the cells to thus detach the cells from the bottom of the compartment.

According to the present invention, the detaching of the adhered cells includes moving a scraper provided in the compartment while the scraper is linked with a unit having magnetic force disposed outside the culture vessel to detach the cells from the bottom of the compartment.

According to the present invention, the obtaining of the cells includes allowing a portion of the detached cells to remain so that the remaining cells are repeatedly propagated in the culture vessel.

According to the present invention, the propagating of the cells in the culture medium includes inoculating the culture medium with the cells and then storing a culture vessel in a culture environment unit while the culture environment unit has a culture temperature of 0 to 42° C. and a gas, required to culture the cells, is supplied to the culture vessel to provide an optimum culture environment, thus culturing the cells.

According to the present invention, the propagating of the cells in the culture medium includes storing a sealed culture vessel in a culture environment unit while the state of a compartment in the sealed culture vessel is converted from a sealed state to an open state and a gas is repeatedly moved out of or into the culture vessel owing to the supply of gas into the culture environment unit and the negative pressure applied to the culture environment unit.

According to the present invention, a sealed culture vessel is selectively opened and closed to an outside, and the culture vessel is drawn from a culture environment unit and conveyed after the compartment of the sealed culture vessel is sealed to the outside.

Advantageous Effects

According to a device for continuously culturing cells and a culturing method using the same of the present invention, the cells and a culture medium are selectively and repeatedly injected, cultured, detached, and obtained while a seal of a culture vessel is maintained, and accordingly, the cells are obtained while some of the cultured cells are allowed to remain during an obtaining process, thereby repeatedly culturing the cells remaining in the culture vessel, preventing the cultured cells from being contaminated, and attaining uniformity of the cultured cells.

Moreover, according to a device for continuously culturing cells and a culturing method using the same of the present invention, an optimum culture temperature and a gas required to propagate the cells are supplied to a culture vessel using a culture environment unit, in which the culture vessel is stored and which provides an optimum culture environment to propagate the cells, thereby improving the efficiency of propagation of cell culture.

Further, according to a device for continuously culturing cells and a culturing method using the same of the present invention, a sealing-type culture vessel is used to easily move, store, and manage the cells.

Figure 1:
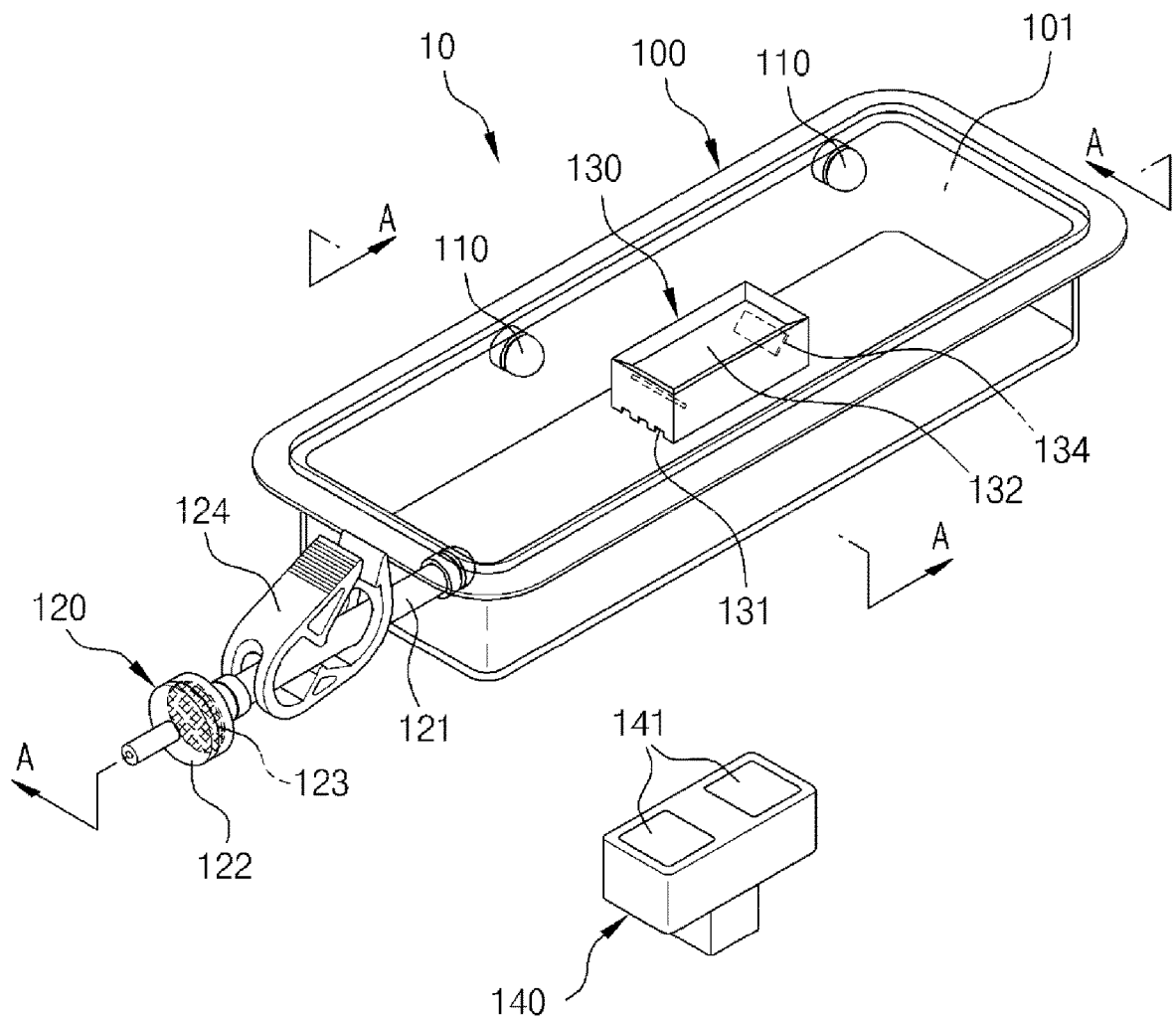
FIG. 1 is a perspective view of a device for continuously culturing cells according to the present invention.

<Description of the Reference Numerals in the Drawings>

| | |
|---|---|
| 10: Culture device | 11: Cell |
| 12: Culture medium | 100: Culture vessel |

-continued

<Description of the Reference Numerals in the Drawings>

| | |
|---|---|
| 101: Space | 110: Sealing-type passageway |
| 120: Circulation filter | 121: Conduit |
| 122: Valve | 123: Filter |
| 124: Clip | 130: Scraper |
| 131: Blade | 132: Culture groove |
| 133: Central axis | 134: Metal body |
| 140: Moving member | 141: Magnetic substance |
| 200: Culture environment unit | |

BEST MODE

Hereinafter, preferred embodiments of the present invention will be described in detail with reference to the accompanying drawings of the present invention.

First, reference should now be made to the drawings, in which the same reference numerals are used throughout the different drawings to designate the same components or parts. In the present invention, a detailed description of known related functions or constitutions will be omitted in order to avoid obscuring the gist of the present invention.

Figure 2:
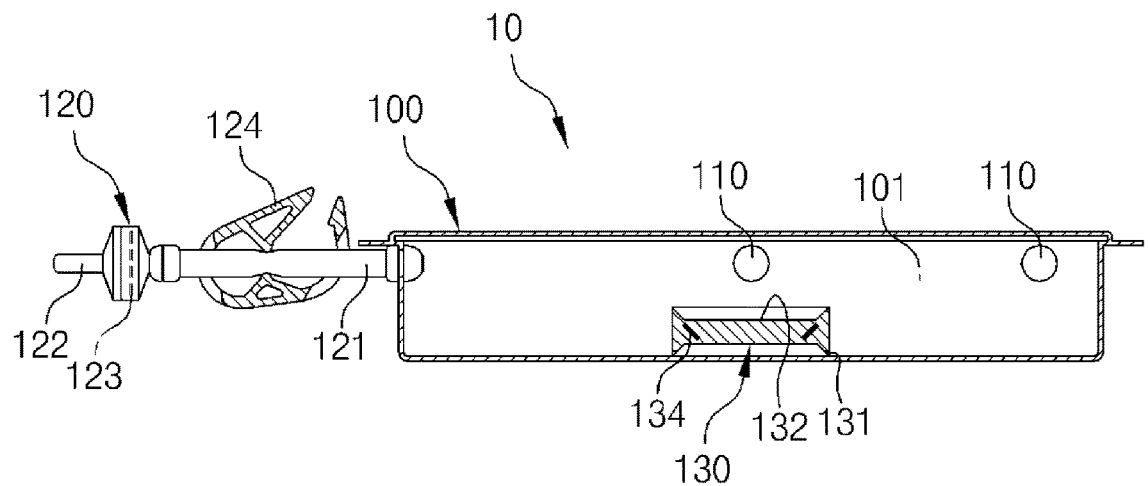
FIG. 2 is a longitudinal sectional view of the device for continuously culturing the cells according to the present invention.
Figure 3:
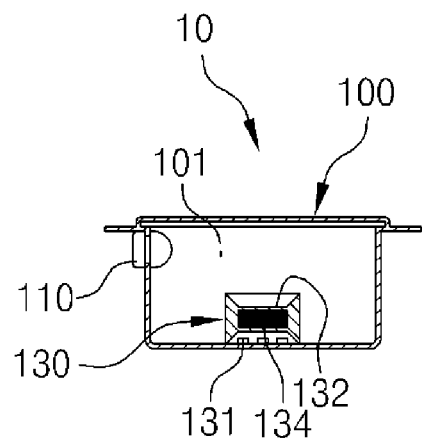
FIG. 3 is a transverse sectional view of the device for continuously culturing the cells according to the present invention.
Figure 8:
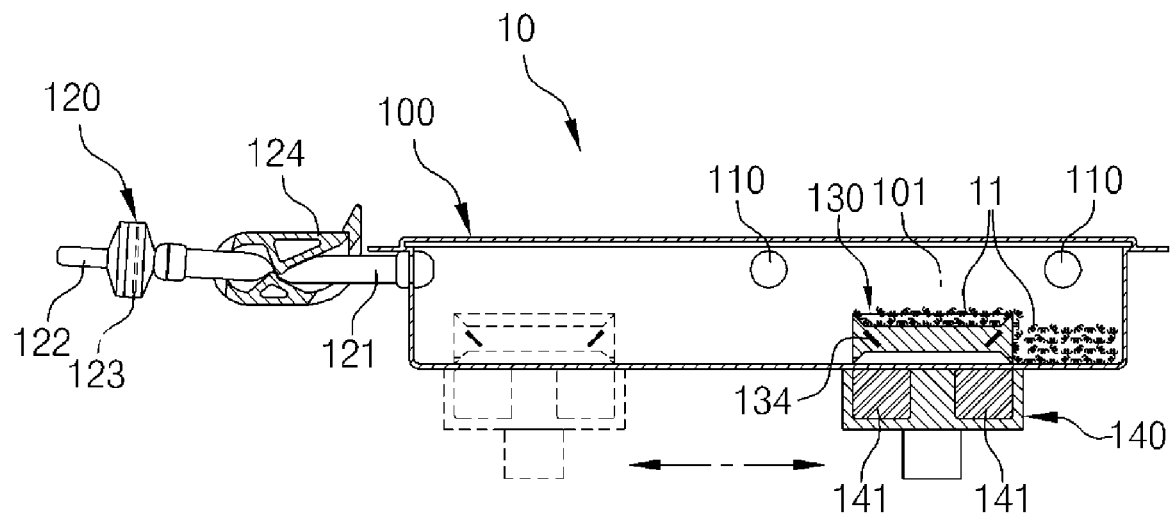
Figure 9:
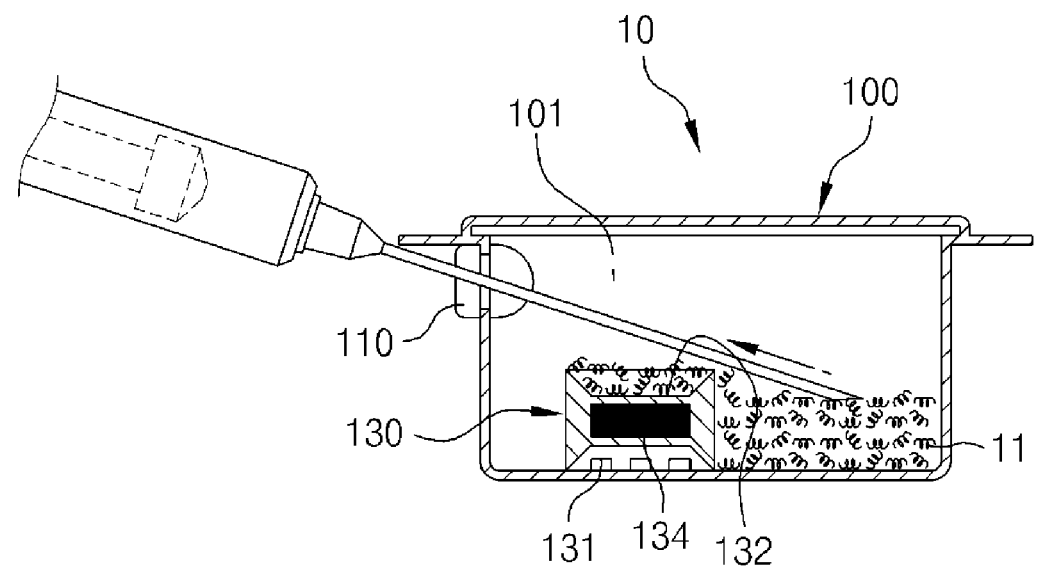
Figure 10:
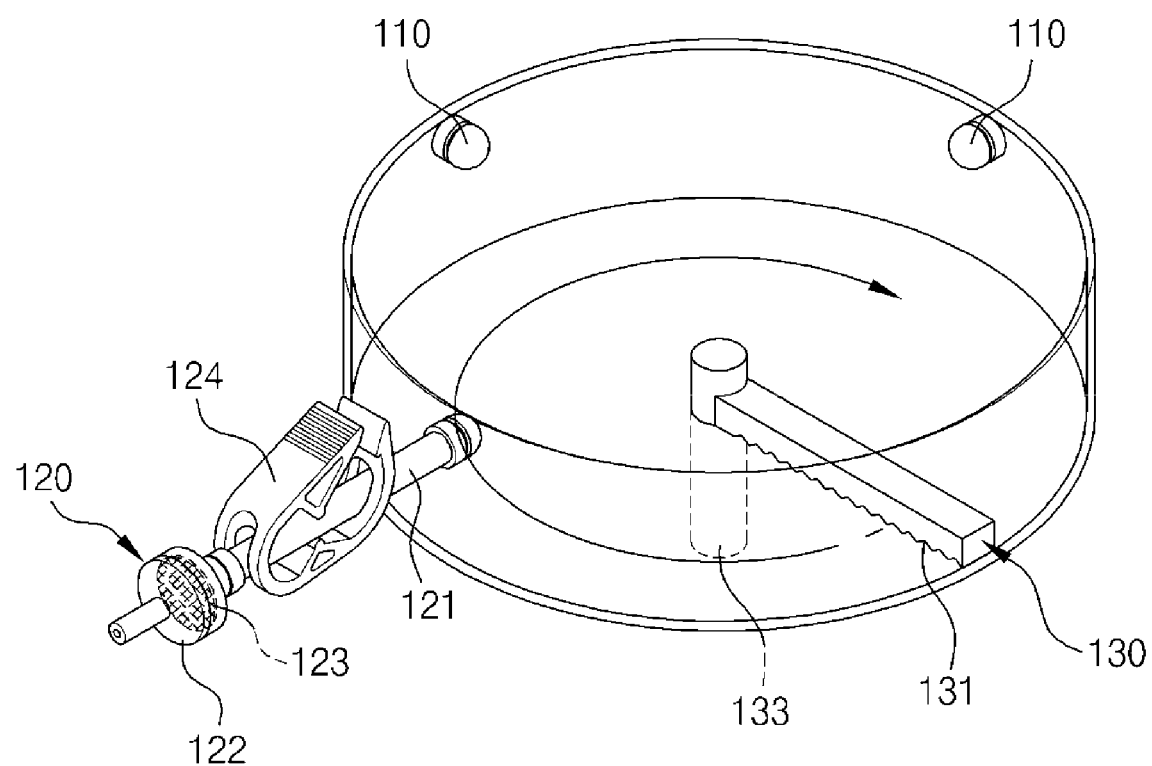
FIG. 10 is a perspective view of a scraper of a device for continuously culturing cells according to another embodiment of the present invention.
Figure 11:
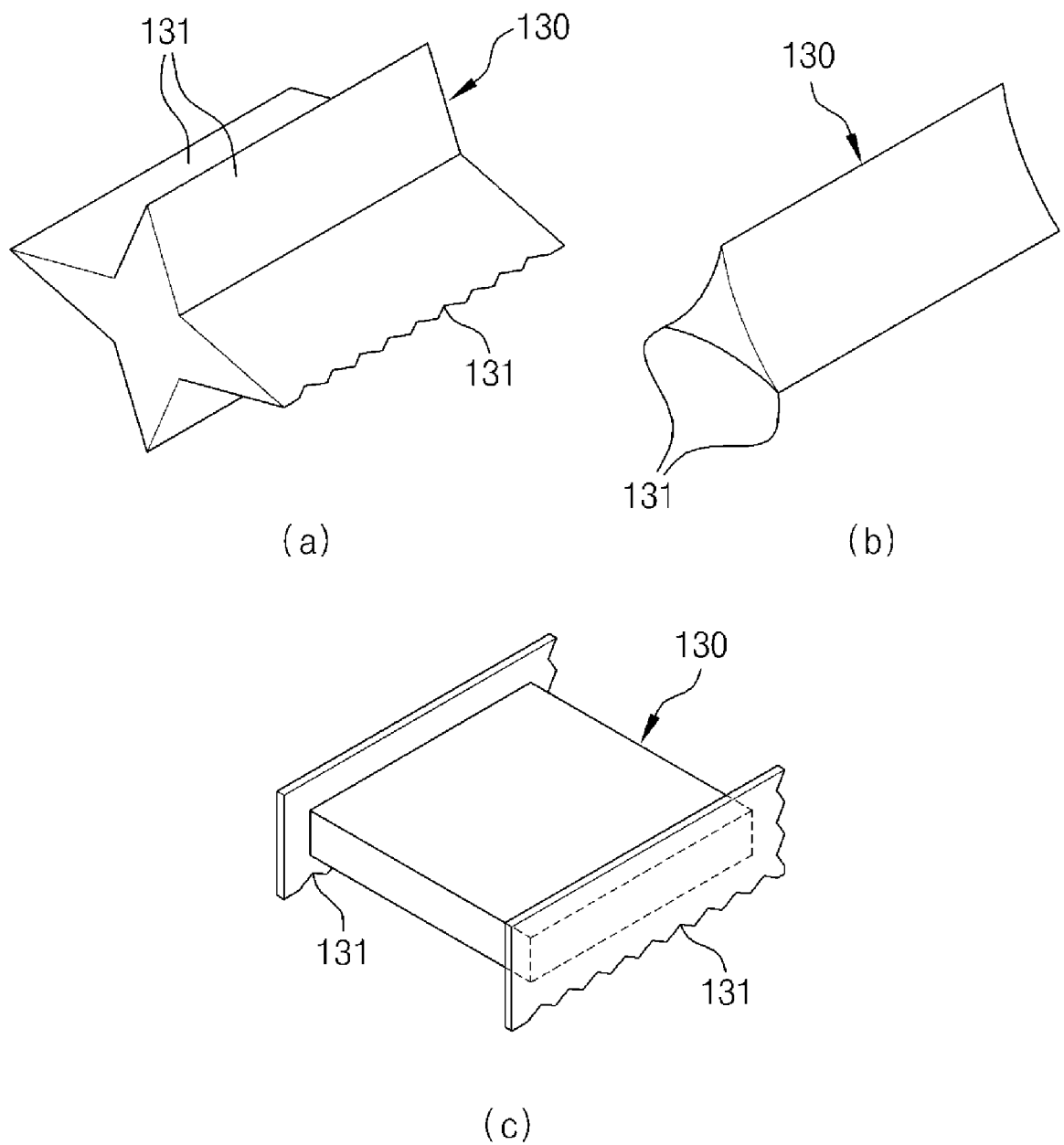
FIG. 11 is a perspective view of a scraper of a device for continuously culturing cells according to various embodiments of the present invention.
Figure 12:
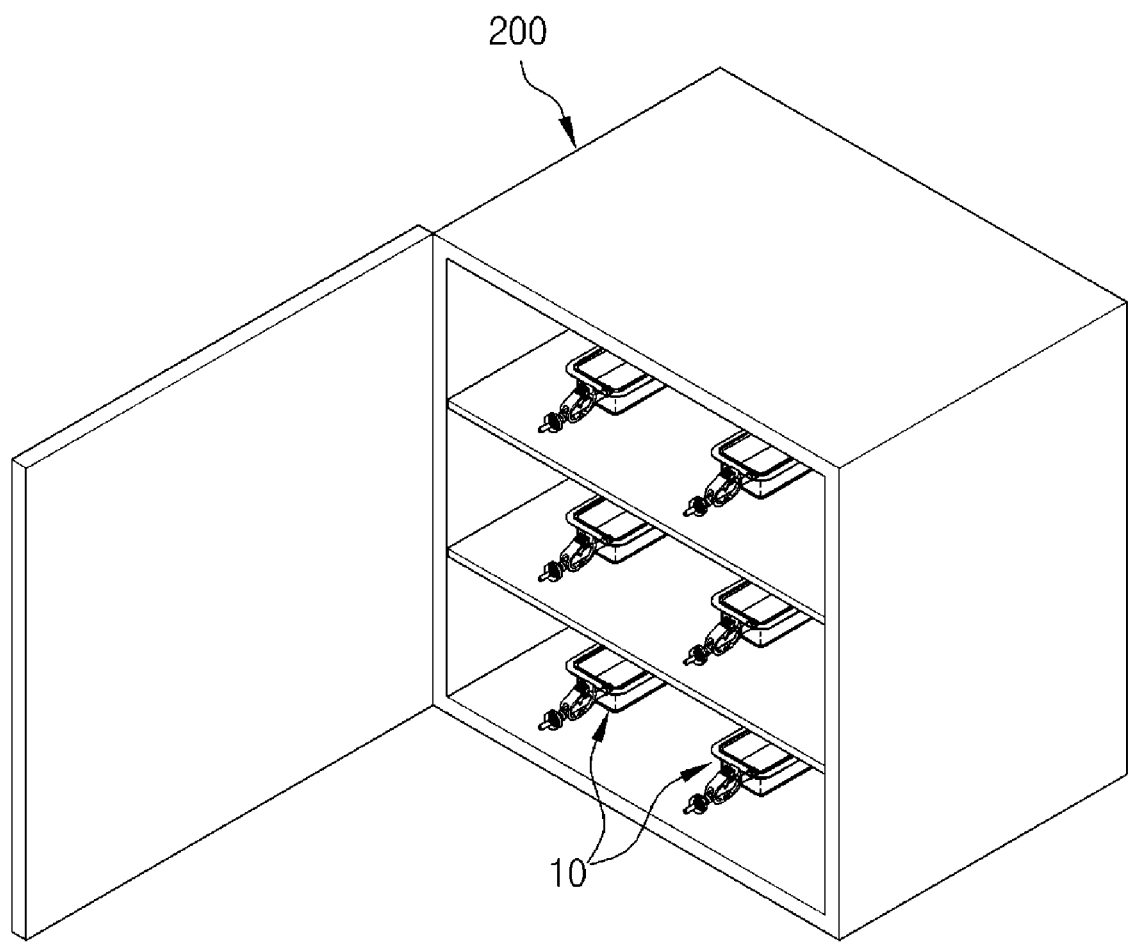
FIG. 12 is a perspective view of a culture environment unit including the device for continuously culturing cells stored therein according to the present invention.
Figure 13:
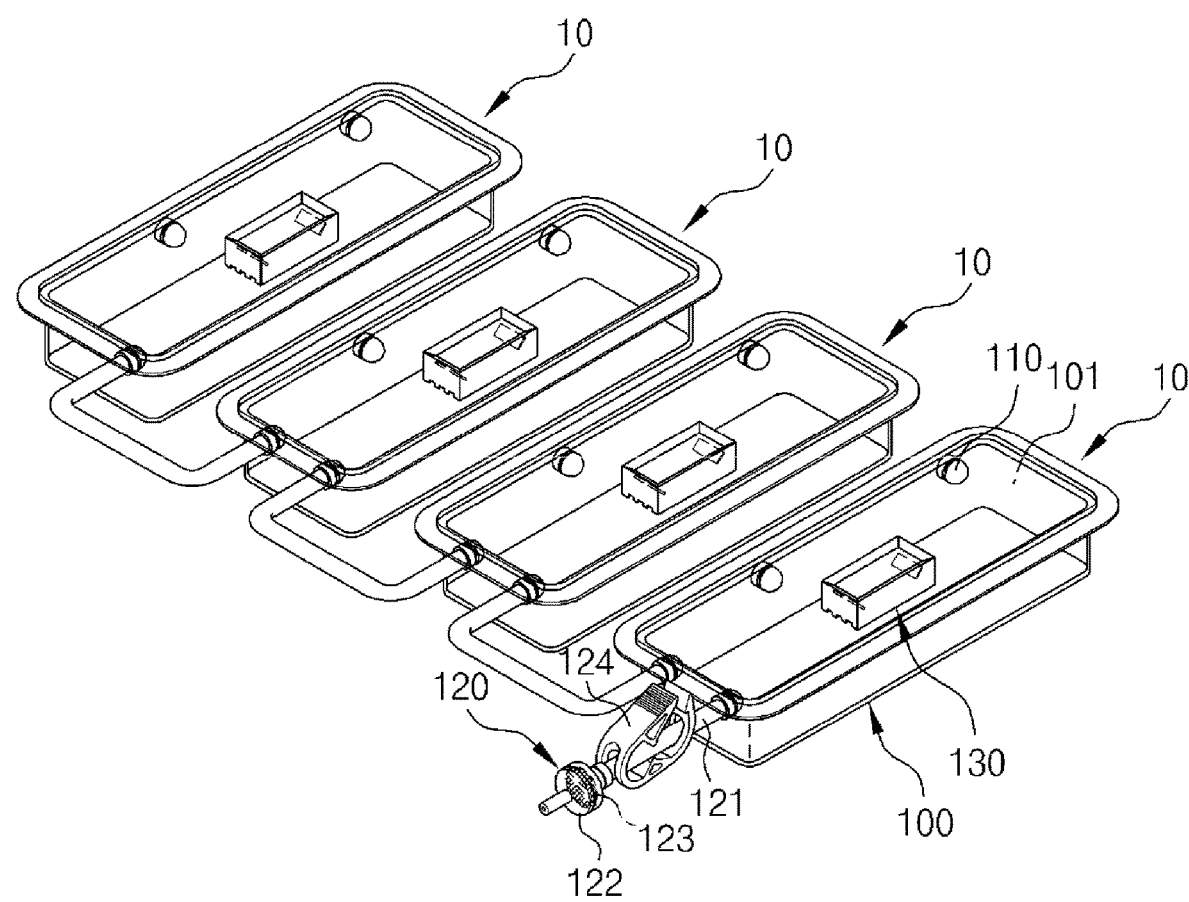
FIG. 13 is a perspective view of a device for continuously culturing cells according to another embodiment of the present invention.

FIG. 1 is a perspective view of a device for continuously culturing cells according to the present invention, FIG. 2 is a longitudinal sectional view of the device for continuously culturing the cells according to the present invention, FIG. 3 is a transverse sectional view of the device for continuously culturing the cells according to the present invention, FIGS. 4 to 9 are flowcharts showing culturing of the cells using the device for continuously culturing the cells according to the present invention, FIG. 10 is a perspective view of a scraper of a device for continuously culturing cells according to another embodiment of the present invention, FIG. 11 is a perspective view of a scraper of a device for continuously culturing cells according to various embodiments of the present invention, FIG. 12 is a perspective view of a culture environment unit including the device for continuously culturing cells stored therein according to the present invention, and FIG. 13 is a perspective view of a device for continuously culturing cells according to another embodiment of the present invention.

First, as shown in FIGS. 1 to 9, for the device for continuously culturing the cells according to the present invention, a polygonal or circular culture vessel 100 is prepared.

A sealed compartment 101 is formed in the culture vessel 100.

The culture vessel 100 may be made of a soft plastic material to enable the size of the compartment 101 to be changed using external pressure or force.

The culture vessel 100 has a compartment that is selectively determined to be sealed, so that a culture medium is injected into the compartment 101 and inoculated with the cells and the cells are detached and obtained while the compartment 101 is sealed and the cells are cultured while the compartment is open.

Further, cells 11 are obtained while some of the cultured cells 11 are allowed to remain during a process of obtaining the cells 11, thereby repeatedly culturing the cells 11 remaining in the culture vessel 100.

Moreover, all of the cultured cells are obtained during the process of obtaining the cells 11, and then injection of the culture medium into the culture vessel 100, inoculation with the cells, and culturing, detaching, and obtaining of the cells are repeated.

A sealing-type passageway 110 and a circulation filter 120 are provided to the culture vessel 100 to continuously culture the cells 11.

First, the sealing-type passageway 110 is provided on the culture vessel 100 to inject a culture medium 12 into the compartment 101, inoculate the culture medium 12 with the cells 11, and obtain the cells 11 therethrough, and the sealed state of the sealed culture vessel is maintained during injection, inoculation, and obtaining.

That is, the sealing-type passageway 110 may be provided on the side surface of the culture vessel 100 to move a fluid, a gas, and the cells 11 from outside into the compartment 101 or from the compartment 101 to the outside therethrough.

The sealing-type passageway 110 is provided on the surface of the culture vessel 100. The sealing-type passageway 110 includes a soft block and communicates with the compartment 101.

Typically, the culture medium 12 and the cells 11 are injected and the cells 11 are obtained to the outside through the sealing-type passageway 110 using a syringe.

In other words, a needle of the syringe is stuck into the sealing-type passageway 110, and the culture medium 12 filling the syringe is then injected into the compartment 101, or the cells 11, which are cultured in the culture vessel 100 and then detached, are drawn into the syringe using the negative pressure of the syringe to obtain the cells 11 to the outside.

Additionally, when the needle is removed from the sealing-type passageway 110 after the culture medium 12 is injected or the cells 11 are obtained, the sealing-type passageway 110 may be sealed by the elasticity of the sealing-type passageway 110 to thus maintain a seal of the compartment 101.

Further, the circulation filter 120 is provided to inject a gas, which is required to culture the cells 11, into the compartment 101 of the culture vessel 100.

That is, the culture vessel 100 is stored in a culture environment unit 200 while the cells 11 are cultured so as to apply an appropriate temperature thereto and receive the gas required to culture the cells 11.

The gas is moved out of or into the compartment 101 in the culture vessel 100 through the circulation filter 120.

That is, as shown in FIG. 13, negative pressure is generated in the culture environment unit 200 to change the size of the compartment 101 of the culture vessel 100 to thus move the gas, which is required to culture the cells 11, out of or into the compartment 101 of the culture vessel 100 in the culture environment unit 200 through the circulation filter 120.

The gas includes one or more of carbon dioxide and oxygen.

The detailed constitution of the circulation filter 120 is as follows.

The circulation filter 120 is constituted by a conduit 121 provided on a side surface of the culture vessel 100, a valve 122 provided at an end of the conduit 121, and a filter 123 provided in the valve 122.

Additionally, a clip 124 is provided around the conduit 121 to selectively seal and open the conduit 121.

When the culture vessel 100 is stored in the culture environment unit 200, the conduit 121 is opened using the clip 124 to move the gas out of or into the compartment 101, and when the culture vessel 100 is moved out of the culture environment unit 200, the conduit 121 is tightened using the clip 124 to seal the compartment 101 of the sealed culture vessel.

Additionally, the cells 11, which are cultured on the bottom surface of the compartment 101 of the culture vessel 100, are not easily detached owing to adhesion force, and accordingly, a scraper 130, which is a separate tool used to detach the cells 11, is provided in the compartment 101.

That is, the scraper 130 scrapes the cells 11 while rotating or moving in the compartment 101 using external mechanical force, magnetic force, or potential energy to detach the cells 11 from the bottom surface of the compartment 101.

Particularly, the scraper 130 is provided in the rectangular culture vessel as shown in FIG. 11, but the shape of the culture vessel is not limited, and may be a circle or a polygon such as a triangle, as long as the culture vessel has a surface to which the cells are capable of adhering.

First, a process of detaching the cells 11 using the scraper 130 and external mechanical force will be described below.

As shown in FIG. 10, a central axis 133 is rotatably provided through the bottom surface of the compartment 101, and is exposed so as to be interlocked with the scraper 130 in the culture vessel 100, so that the scraper 130, which rotates depending on the rotation of the central axis 133, is rubbed on the bottom surface of the compartment 101 to detach the cells 11 by scraping.

When the cells 11 are detached using the rotation of the scraper 130, the culture vessel 100 has a cylinder shape, and the scraper 130 is rotated around the central axis 133 along the internal circumference of the compartment 101 to detach the cells 11.

Further, a process of detaching the cells 11 using magnetic force will be described below.

A moving member 140, which is separately provided, is moved so as to come close to the external lower surface of the culture vessel 100, the scraper 130 and the moving member 140 are linked using magnetic force, and the scraper 130 is rubbed in the compartment 101 according to the movement of the moving member 140 so as to detach the cells 11 by scraping.

That is, the scraper 130 and the moving member 140 may include a metal body 134 or a magnetic substance 141 so as to be integrally linked with each other using magnetic force.

Additionally, in the process of detaching the cells using potential energy, the culture vessel 100 is oriented at an angle to allow the scraper 130 to slip on the bottom surface of the compartment 101 due to its own weight, thus detaching the cells 11 by scraping.

The scraper 130 having the aforementioned constitution has a culture groove 132 in the upper side thereof to fill the culture groove with the culture medium 12 and culture the cells 11 in the culture groove.

That is, in the device for continuously culturing the cells 11 according to the present invention, the culture medium 12 is injected into the compartment 101 or into the compartment 101 and the culture groove 132 in the scraper 130 to inoculate the culture medium 12 with the cells 11.

Additionally, a plurality of blades 131 is formed on the lower surface of the scraper 130, which comes into contact with the bottom surface of the compartment 101.

The plurality of blades 131 is formed on the lower surface of the scraper 130, which comes into contact with the bottom surface of the compartment 101, and the blades 131 are formed so as to have an edge angle to thus detach the cells 11 from the bottom surface by rubbing the bottom surface of the compartment 101.

Alternatively, the plurality of blades 131 is formed on the lower surface of the scraper 130, which comes into contact with the bottom surface of the compartment 101, and the blades 131 are formed so as to have continuous edge angles to thus come into contact or not come into contact with the bottom surface of the compartment 101.

Further, the scraper is made of a material selected from polyethylene (PE), polypropylene (PP), polyamide (PA), polyacetal (POM), polyvinyl chloride (PVC), polyester (PET), polymethylpentene (PMP), an ionomer (IO), ethylene vinyl alcohol (EVOH), polystyrene (PS), a methacrylic resin (PMMA), polycarbonate (PC), polyvinyl acetate (PVAc), polyvinyl alcohol (PVA), a phenol resin (PF), a urea resin (UF), a melamine resin (MF), an epoxy resin (EP), polyurethane (PUR), an unsaturated polyester resin (UP), and a metal.

One or more culture vessels 100 having the aforementioned constitution are provided, and continuously connected in parallel with each other through the circulation filter 120.

That is, as shown in FIG. 13, a plurality of culture vessels 100 is sequentially arranged, and the culture vessels 100, which are arranged to be adjacent to the culture vessel 100 positioned at one side as a basis, are sequentially connected to the circulation filter 120 to integrally move the gas out of or into the plurality of culture vessels 100 through the circulation filter 120 of the culture vessel 100 positioned at one side.

A method of continuously culturing the cells using the culture device having the aforementioned constitution will be described below.

The method includes culturing the cells 11 by injecting the culture medium 12 into the internal compartment 101 of the sealed culture vessel 100 and then inoculating the culture medium 12 with the cells 11, detaching the adhered cells 11 when the density of the cells 11 cultured in the compartment 101 of the culture vessel 100 is a reference value or more, and obtaining the cells 11 detached from the culture vessel 100, which is maintained in a sealed state.

Figure 4:
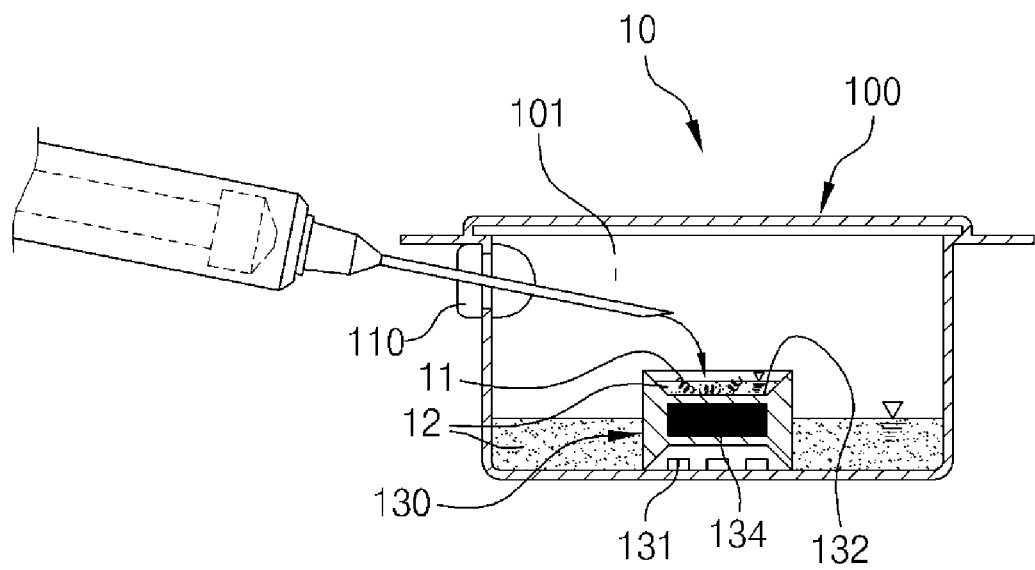
FIGS. 4 to 9 are flowcharts showing culturing of the cells using the device for continuously culturing the cells according to the present invention.
Figure 5:
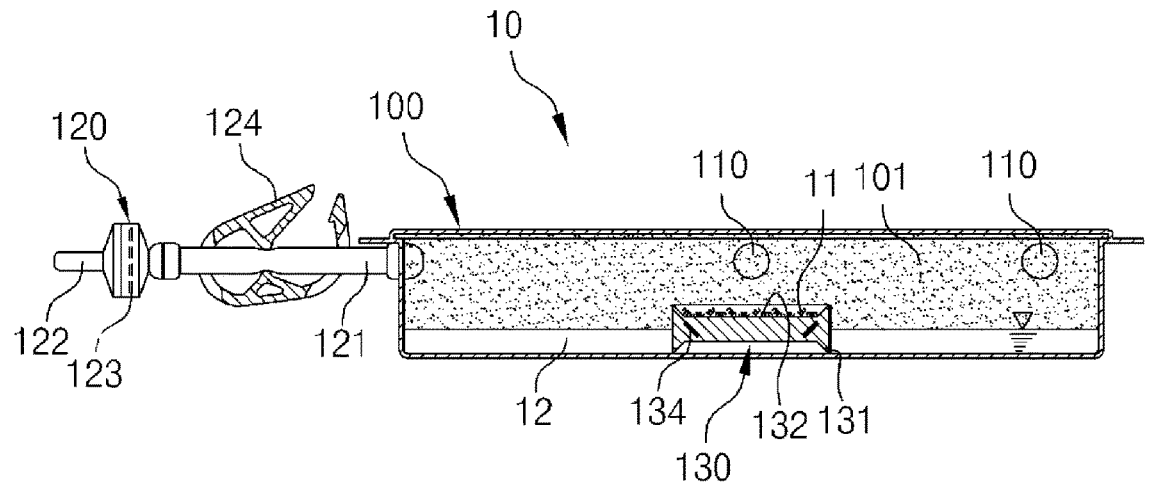

First, as shown in FIG. 4, the culturing of the cells includes, in detail, injecting the culture medium 12 into the compartment 101, inoculating the culture medium 12 with the cells 11, and propagating the cells 11 in the culture medium 12.

During the propagation of the cells 11 in the culture medium 12, the culture medium 12 is inoculated with the cells 11 and then the culture vessel is stored in the culture environment unit 200 to culture the cells.

The culture environment unit 200 has a culture temperature of 0 to 42° C., and the gas required to culture the cells 11 is supplied to the culture vessel.

Further, pressure from the clip is removed from the circulation filter so as to open the conduit.

Figure 6:
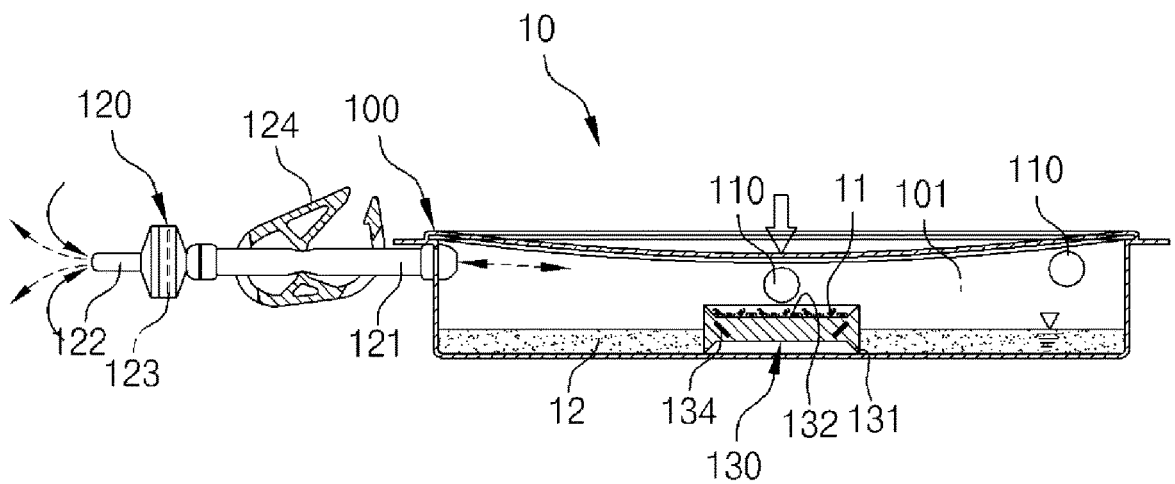
Figure 7:
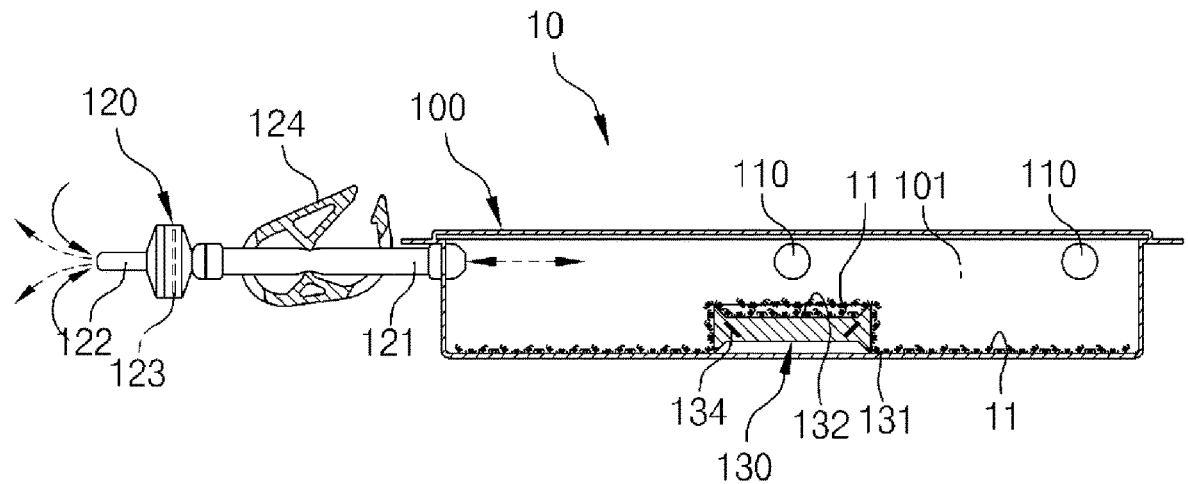

The gas required to culture the cells 11 is supplied into the culture environment unit 200, and negative pressure is repeatedly generated in the culture environment unit 200 to repeatedly move the gas out of or into the culture vessel 100. That is, as shown in FIG. 6, the culture vessel 100 is made of a soft material that is influenced by external pressure, in this case negative pressure, to thus change the size of the compartment 101.

The compartment 101 is then elastically restored to its original form to draw the gas present in the culture environment unit 200, thereby moving the gas out of or into the compartment 101.

The gas is moved out of or into the compartment 101 through the circulation filter 120 provided to the culture vessel 100.

Particularly, the clip 124 may be provided in the circulation filter 120 to selectively tighten or loosen around the circulation filter 120, thereby determining opening or closing of the circulation filter 120.

After the cells 11 are propagated in the culture vessel 100 in the culture environment unit 200, in order to obtain the cells 11, the circulation filter 120 is sealed using the clip 124 to seal the culture vessel 100.

Next, as shown in FIG. 8, after the culture vessel 100 is moved out of the culture environment unit 200, when the scraper 130 and the moving member 140, having a magnetic force function, come into close contact with the lower surface of the culture vessel 100 and are then moved, the scraper 130, positioned in the compartment 101, is linked with the moving member 140 to detach the cells 11 adhered to the bottom surface of the compartment 101 by scraping.

Alternatively, during the detaching of the cells 11, the scraper 130 provided in the compartment 101 is rotated and moved using mechanical energy to detach the cells 11 from the bottom of the compartment 101 by scraping.

That is, the scraper 130 is rotatably combined with the compartment 101 through the central axis 133, and the central axis 133 is exposed to be interlocked with the scraper 130 in the compartment 101 and rotated to thus detach the cells 11 from the bottom surface of the compartment 101 by scraping.

Alternatively, the scraper 130 is moved using potential energy to detach the cells 11 from the bottom surface of the compartment 101 by scraping.

That is, the culture vessel 100 is oriented at an angle so as to allow the scraper 130 to slip on the bottom surface of the compartment 101 due to its intrinsic weight, thus detaching the cells 11 by scraping.

Subsequently, the needle of the syringe is stuck into one of the sealing-type passageways 110 other than the sealing-type passageway 110 into which the culture medium is injected, so as to draw the cultured cells 11 through the needle into the syringe using the negative pressure of the syringe, thereby obtaining the cells.

As shown in FIG. 9, some of the detached cells 11 are allowed to remain during the obtaining of the cells 11, so that the remaining cells 11 are repeatedly propagated.

INDUSTRIAL APPLICABILITY

As described above, in the method of continuously culturing the cells 11 according to the present invention, the injecting of the culture medium 12, the inoculating of the culture medium 12 with the cells 11, the culturing of the cells 11, the detaching of the cells 11, and the obtaining of the cells 11 are performed while the sealed culture vessel is always sealed so as to stably and repeatedly culture the cells 11 after the obtaining of the cells 11.

The foregoing present invention is not limited to the foregoing examples and the accompanying drawings. It will be apparent to those skilled in the art that various substitutions, modifications, and changes may be made without departing from the technical spirit of the invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A device for continuously culturing cells, comprising:
a culture vessel having a compartment inside of which cells are capable of being cultured, the culture vessel comprising a top surface, a bottom surface and a side surface, the culture vessel being formed of a plastic material so as to be able to change a size of the compartment by an internal pressure or an external force;

a sealing passageway formed in the culture vessel, the sealing passageway including a soft block through which the cells and a culture medium are capable of being injected into the compartment and cultured cells are capable of being removed from the compartment, using a syringe;

a circulation filter formed in the culture vessel, the circulation filter including a conduit through which a gas required to culture the cells is able to be circulated into the compartment, a filter provided inside the conduit, and a clip provided around the conduit to selectively close or open the conduit;

a scraper movably disposed on the bottom surface of the culture vessel, the scraper including a culture groove formed on a top surface of the scraper, a metal body, and a blade formed on a bottom surface of the scraper; and a moving member including a magnetic substance, the moving member being detachably attached to the scraper from outside of the culture vessel by the magnetic substance and the metal body, wherein, when the moving member moves, the scraper moves along the bottom surface of the culture vessel and scrapes the cultured cells by the blade of the scraper, wherein the culture vessel is sealed by the top surface, the bottom surface and the side surface when the conduit is closed by the clip, thereby being able to inject the cells and the culture medium into the compartment and remove the cultured cells from the compartment through the sealing passageway while continuously culturing the cells.

2. The device of claim 1, wherein the sealing passageway includes: one or more sealing passageways provided in the side surface of the culture vessel, and the soft block is configured to seal the sealing passageway when a needle of the syringe is stuck into the compartment and moved out of the compartment by means of elasticity of the soft block.

3. The device of claim 1, wherein the circulation filter further includes: a valve provided at an end of the conduit, and the filter provided inside the valve.

4. The device of claim 1, wherein the culture vessel is configured to be connected to neighboring other culture vessels through the conduit of the circulation filter.

5. The device of claim 1, wherein the scraper is made of a material selected from the group consisting of polyethylene (PE), polypropylene (PP), polyamide (PA), polyacetal (POM), polyvinyl chloride (PVC), polyester (PET), polymethylpentene (PMP), an ionomer (IO), ethylene vinyl alcohol (EVOH), polystyrene (PS), a methacrylic resin (PMMA), polycarbonate (PC), polyvinyl acetate (PVAc), polyvinyl alcohol (PVA), a phenol resin (PF), a urea resin (UF), a melamine resin (MF), an epoxy resin (EP), polyurethane (PUR), an unsaturated polyester resin (UP), and a metal.

6. The device of claim 1, wherein the blade of the scraper includes: two or more blades, and the two or more blades are formed so as to have an edge angle to thus detach the cultured cells from the bottom surface of the culture vessel.

7. The device of claim 1, wherein the blade of the scraper includes: two or more blades, and the two or more blades are formed so as to have continuous edge angles to thus come into contact or not come into contact with the bottom surface of the culture vessel.

* * * * *